United States Patent
Zenati et al.

(10) Patent No.: US 7,709,081 B2
(45) Date of Patent: May 4, 2010

(54) POROUS BIOACTIVE GLASS AND PREPARATION METHOD THEREOF

(75) Inventors: Rachid Zenati, Neuville sur Saone (FR); Gilbert Fantozzi, Meyzieu (FR); Jerome Chevalier, Rillieux-la-Pape (FR); Mourad Arioua, Lyons (FR)

(73) Assignee: Institut National des Sciences Appliques (INSA), Villeurbanne (FR)

( * ) Notice: Subject to any disclaimer, the term of this patent is extended or adjusted under 35 U.S.C. 154(b) by 410 days.

(21) Appl. No.: 11/658,161

(22) PCT Filed: Jul. 25, 2005

(86) PCT No.: PCT/FR2005/001921

§ 371 (c)(1),
(2), (4) Date: Feb. 1, 2007

(87) PCT Pub. No.: WO2006/018531

PCT Pub. Date: Feb. 23, 2006

(65) Prior Publication Data

US 2008/0038534 A1  Feb. 14, 2008

(30) Foreign Application Priority Data

Jul. 27, 2004  (FR) ................... 04 08288

(51) Int. Cl.
| B32B 17/06 | (2006.01) |
| B32B 3/00 | (2006.01) |
| C03C 3/076 | (2006.01) |
| C03B 19/01 | (2006.01) |

(52) U.S. Cl. .............. 428/315.5; 428/307.3; 428/316.6; 428/312.8; 428/312.6; 428/426; 501/53; 501/55; 501/63; 501/69; 501/70; 65/17.3; 65/17.5

(58) Field of Classification Search ........................ None
See application file for complete search history.

(56) References Cited

U.S. PATENT DOCUMENTS

2001/0014355 A1  8/2001  Ducheyne et al.
2003/0138473 A1  7/2003  Koblish et al.
2004/0241238 A1*  12/2004  Sepulveda et al. .......... 424/486

FOREIGN PATENT DOCUMENTS

| EP | 0 401 793 A1 | 12/1990 |
| WO | WO-99/07777 | * 2/1999 |
| WO | WO 02/096391 A1 | 12/2002 |

OTHER PUBLICATIONS

Lin et al., "Fabrication and biocompatibility of a porous bioglass ceramic in a $Na_2O$-$CaO$-$SiO_2$-$P_2O_5$ system," *Journal of Biomedical Engineering*, vol. 13, No. 4, pp. 328-334 (1991).

Kaufmann et al., "Effect of varying physical properties of porous, surface modified bioactive glass 45S5 on osteoblast proliferation and maturation," *Journal of Biomedical Materials Research*, vol. 52, No. 4, pp. 783-796 (2000).

Gong et al., "Porous bioactive glass and glass-ceramics made by reaction sintering under pressure," *Journal of Biomedical Materials Research*, vol. 54, No. 3, pp. 320-327 (2000).

* cited by examiner

*Primary Examiner*—Ling Xu
(74) *Attorney, Agent, or Firm*—Oliff & Berridge, PLC (57) ABSTRACT

The invention relates to porous bioglass and to the preparation method thereof. More specifically, the invention relates to a solid, porous crystalline or partially-crystalline composition containing at least $SiO_2$, $CaO$, $Na_2O$, and $P_2O_5$, comprising micropores and macropores. The invention is characterised in that: the pore ratio varies between 50% and 80%, preferably between 60 and 75%, and is measured using the geometric method; the average diameter of the macropores varies between 100 and 1250 micrometers, preferably between 150 and 300 micrometers; the average diameter of the micropores is less than or equal to 5 micrometers; and the compression strength varies between 7 MPa and 70 MPa. The invention also relates to the method of preparing one such composition and to such a composition treated with a physiological liquid having an ionic composition similar to that of human plasma. The invention also relates to an implant which is made from one such composition.

23 Claims, 8 Drawing Sheets

POROUS BIOACTIVE GLASS AND PREPARATION METHOD THEREOF

The present invention relates to a porous, crystalline or partially crystalline composition, or bioactive glass, that is particularly mechanically resistant and can be used as a bone substitute.

In the field of synthetic bone substitutes, implants based on hydroxyapatite and tricalcium phosphate are well-known and have been used for many years. Hydroxyapatite is a calcium phosphate ceramic with a composition close to the mineral part of natural bone. It is this which allows short-term healing, from the surface of the implant. However, hydroxyapatite is not resorbable and in the long term remains in the body of the patient. In order to limit this drawback, tricalcium phosphate is added to it, which is a resorbable calcium phosphate that allows bone to take its place, in order to restore bone to the implant in the long term.

The implants combining hydroxyapatite and tricalcium phosphate are thus considered as the main alternative to autografts, the latter not always being possible. However, contrary to bone autograft, these implants based on hydroxyapatite and tricalcium phosphate are not osteoinducers, that is to say that they do not promote the development of bone cells within the implant.

Another drawback of the existing implants is that they are difficult to handle and to use in bulk form. Thus, a mass of hydroxyapatite/tricalcium phosphate ceramic is difficult for the surgeon to cut to the desired shape at the time of the operation, because it is too hard and friable.

To remedy this drawback, the bony substitutes based on hydroxyapatite are sometimes supplied in the form of granules. The surgeon fills the cavity that is to be filled in with these granules. However, this technique is delicate and requires a retaining cage in order to avoid any spread outside of the site to be treated. The granules may crumble or cause injuries with their fragments.

It has therefore been desired to develop bone substitutes based on porous hydroxyapatite in order to make them easier to handle and cut. However, a major drawback of these bone substitutes is their brittleness. Indeed, due to the presence of collagen, natural bone is ductile and strong. On the contrary, porous implants based on hydroxyapatite and tricalcium phosphate break and crumble easily. Thus, it is very difficult for a surgeon to cut out a particular shape from a porous mass of hydroxyapatite/tricalcium phosphate-based bone substitute without the mass crumbling.

The article "Effect of varying physical properties of porous, surface modified bioactive glass 45S5 on osteoblast proliferation and maturation", E. A. B. Effah Kaufmann, P. Ducheyne, I. M. Shapiro, Journal of Biomedical Materials Research, 2000, vol. 52, No. 4, pp. 783-796, describes a porous bioactive glass promoting the development of bone cells after implantation. However, this porous bioactive glass is extremely brittle. It does not have good mechanical strength and crumbles when attempts are made to cut it to create a particular shape of implant.

Similarly, the article "Porous bioactive glass and glass-ceramic made by reaction sintering under pressure", Weiliang Gong, Abdesselam Abdelouas, Werner Lutze, Journal of Biomedical Materials Research, 2001, vol. 54, No. 3, pp. 320-327, describes glasses and glass-ceramics prepared by sintering under isostatic pressure. However, these compositions have a low degree of porosity which makes them difficult to handle and to cut. In addition, the development of bone cells is not promoted.

Thus there is a need for a porous bulk bioactive glass, capable of promoting the development of bone cells in vivo after implantation in the human body by substitution of natural bone, and having mechanical properties that allow this bioactive glass to be cut into the desired shape without it losing its integrity.

The present invention aims to solve this problem by providing a porous crystalline or semicrystalline composition based on the $SiO_2$, $CaO$, $Na_2O$ and $P_2O_5$ system comprising macropores and micropores of particular sizes respectively and a specific degree of porosity, and having a compressive strength ranging from 7 MPa to 70 MPa.

A first subject of the present invention is a bulk porous, crystalline or partially crystalline composition comprising at least $SiO_2$, $CaO$, $Na_2O$ and $P_2O_5$, comprising micropores and macropores, characterized in that:

the degree of porosity ranges from 50% to 80%, measured by the geometric method;

the average diameter of the macropores ranges from 100 to 1250 microns, preferably from 150 microns to 300 microns;

the average diameter of the micropores is less than or equal to 5 microns; and the compressive strength ranges from 7 MPa to 70 MPa.

Another subject of the invention is an implant characterized in that it is made from a composition such as above.

Another subject of the present invention is a method for preparing a bulk porous, crystalline or partially crystalline composition comprising at least $SiO_2$, $CaO$, $Na_2O$ and $P_2O_5$, comprising micropores and macropores, of which the degree of porosity ranges from 50% to 80% measured by the geometric method, the average diameter of the macropores ranging from 100 to 1250 microns, preferably 150 microns to 300 microns, the average diameter of the micropores being less than or equal to 5 microns, characterized in that it comprises the following steps:

a) a glass based on $SiO_2$, $CaO$, $Na_2O$ and $P_2O_5$ is used;

b) the glass from step a) is ground and sieved to obtain a powder;

c) the powder obtained in b) is suspended in a solvent and dispersed using a dispersant in order to obtain a slurry;

d) a thickening agent is added to the slurry obtained in c);

e) the mixture obtained in d) is poured into a mold then dried to give a "cake";

f) the "cake" obtained in e) is heated at a temperature of about 600° C. in order to obtain a "green body"; and g) the green body obtained in f) is treated at a temperature ranging from 600° C. to 1100° C., preferably from 900° C. to 1100° C., in order to obtain partial or total crystallization of the composition.

Another subject of the invention is a composition capable of being obtained according to the method above.

The composition according to the invention has a mechanical strength allowing particular shapes to be cut from its mass without the latter crumbling or losing its integrity, and this despite its high degree of porosity. Thus, the composition according to the invention is easy to handle. The surgeon may simply and easily cut it, possibly recut it, to the desired shape before implanting it.

It is possible to cut implants of any shape desired from the composition according to the invention, for example to fill in a bone defect.

Since the implant produced is then a single part, it is particularly strong and stable. It does not generate undesirable fragments.

The composition according to the invention has a homogeneous porosity. This is shown, in particular, from the low spread of compressive strength measurements of these compositions. The presence of micropores promotes the adhesion of the cells. The presence of macropores promotes the penetration of the cells, in particular of the large-size cells.

In addition, the implants produced from the composition according to the invention are resorbable. Thus, they are quite compatible with in vivo use as an implant, in particular as a bone substitute. In addition, they promote the development of bone cells. In the long term, the implant is thus replaced by natural bone.

Lastly, due to their porosity, the implants produced from the composition of the invention are particularly light, which is a comfort for the patient and for the surgeon.

The term "bioactive glass" is understood to mean, in the context of the present invention, a partially or completely recrystallized glass that is compatible with the human body and is bioactive, that is to say capable of developing a biological response at the interface between said glass and human tissue, and therefore of developing a bond between said glass and said human tissue.

The term "bulk" composition is understood to mean, in the context of the present invention, a three-dimensional solid composition, from which it is possible to cut the implants, and not a pulverulent composition.

The present invention will now be described in further detail below.

The composition according to the invention comprises at least $SiO_2$, CaO, $Na_2O$ and $P_2O_5$. The composition may, in addition, comprise a component chosen from $K_2O$, MgO, $Al_2O_3$, $CaF_2$, $B_2O_3$ and mixtures thereof.

In a preferred embodiment of the invention, $SiO_2$ is present in the composition in an amount ranging from 40% to 55% by weight, relative to the total weight of the composition, CaO is present in the composition in an amount ranging from 15% to 25% by weight, relative to the total weight of the composition, $Na_2O$ is present in the composition in an amount ranging from 15% to 25% by weight, relative to the total weight of the composition and $P_2O_5$ is present in the composition in an amount ranging from 1% to 9% by weight, relative to the total weight of the composition.

$K_2O$ may, for example, be present in the composition in an amount ranging from 0.1 to 8% by weight, relative to the total weight of the composition. MgO may, for example, be present in the composition in an amount ranging from 0.1 to 5% by weight, relative to the total weight of the composition. $Al_2O_3$ may, for example, be present in the composition in an amount ranging from 0.1 to 1.5% by weight, relative to the total weight of the composition. $CaF_2$ may, for example, be present in the composition in an amount ranging from 0.1 to 12.5% by weight, relative to the total weight of the composition. $B_2O_3$ may, for example, be present in the composition in an amount ranging from 0.1 to 10% by weight, relative to the total weight of the composition.

More preferably, the composition is made of 45% by weight of $SiO_2$, relative to the total weight of the composition, 24.5% by weight of CaO, relative to the total weight of the composition, 24.5% by weight of $Na_2O$, relative to the total weight of the composition and 6% by weight of $P_2O_5$, relative to the total weight of the composition. Such a composition particularly promotes the development of bone cells.

The composition according to the invention is porous and has a degree of porosity ranging from 50% to 80% measured by the geometric method, preferably from 60 to 75%. In this method, the degree of porosity T is given by the equation:

$$T=1-(\text{bulk density/theoretical density})$$

in which the bulk density is determined by the geometric method. This density is calculated according to the formula $\rho=m/V$ in which:

$\rho$ is the density ($g/cm^3$), m is the mass of the sample (g); and

V is the volume of the sample ($cm^3$).

The theoretical density of the material is estimated to be about 2.75 $g/cm^3$, regardless of the oxide composition.

The average diameter of the macropores ranges from 100 to 1250 microns, preferably from 150 microns to 300 microns. Thus, the large-size cells, such as osteocytes, may penetrate into the implant through interconnections of sufficient size. The average diameter of the micropores is less than or equal to 5 microns. Thus, the adhesion of the cells and also the circulation of biological fluids are particularly promoted.

The composition according to the invention has a compressive strength ranging from 7 MPa to 70 MPa, preferably from 25 MPa to 70 MPa.

Throughout the present application, the compressive strength is measured according to the following method: samples of compositions according to the invention are prepared in the form of cylinders with a diameter of 9 mm and a height of 6 mm. The compressive strength test is carried out using a hydraulic Instron® 8512 machine having a 5000 N load cell. The load is applied to the sample with a strain rate of 1 mm/min. and the force required to break the sample is measured. This force corresponds to the compressive strength of the composition.

In a preferred embodiment of the invention, the composition according to the invention has a compressive strength, measured according to this method, of about 7 MPa, for a degree of porosity, measured according to the geometric method, of about 75%.

In another preferred embodiment of the invention, the composition according to the invention has a compressive strength measured according to this method, of about 70 MPa, for a degree of porosity, measured according to the geometric method, of about 50%.

The compositions according to the invention are preferably prepared by the method which will now be described below.

In a first step, step a) a glass based on $SiO_2$, CaO, $Na_2O$ and $P_2O_5$ is used. The glass in step a) may, in addition, comprise a component chosen from $K_2O$, MgO, $Al_2O_3$, $CaF_2$, $B_2O_3$ and mixtures thereof.

In a preferred embodiment of the method of the invention, $SiO_2$ is present in the glass in an amount ranging from 40% to 55% by weight, relative to the total weight of the glass, CaO is present in the glass in an amount ranging from 15% to 25% by weight, relative to the total weight of the glass, $Na_2O$ is present in the glass in an amount ranging from 15% to 25% by weight, relative to the total weight of the glass and $P_2O_5$ is present in the glass in an amount ranging from 1% to 9% by weight, relative to the total weight of the glass.

$K_2O$ may, for example, be present in the glass in an amount ranging from 0.1 to 8% by weight, relative to the total weight of the glass. MgO may, for example, be present in the glass in an amount ranging from 0.1 to 5% by weight, relative to the total weight of the glass. $Al_2O_3$ may, for example, be present in the glass in an amount ranging from 0.1 to 1.5% by weight, relative to the total weight of the glass. $CaF_2$ may, for example, be present in the glass in an amount ranging from 0.1 to 12.5% by weight, relative to the total weight of the glass. $B_2O_3$ may, for example, be present in the glass in an amount ranging from 0.1 to 10% by weight, relative to the total weight of the glass.

Preferably, this glass is made of 45% by weight of $SiO_2$, relative to the total weight of the glass, 24.5% by weight of CaO, relative to the total weight of the glass, 24.5% by weight of $Na_2O$, relative to the total weight of the glass and 6% by weight of $P_2O_5$, relative to the total weight of the glass. Such a glass is commercially available under the name "45S5®" from Orthovita.

Alternatively, the glass in step a) may be manufactured according to any known method for manufacturing a glass, such as for example the sol-gel method or else by simple melting. The sol-gel method conventionally comprises a step of mixing metal oxides in solution, then a hydrolysis step, followed by gelling and treating at a temperature generally ranging from 600° C. to 900° C. in order to produce a glass. The melting method conventionally comprises a step of mixing oxide powders, melting and homogenizing the mixture at a temperature generally ranging from 1250° C. to 1600° C., then cooling in order to obtain an amorphous glass.

In a second step, step b), the glass in step a) is ground and sieved to obtain a powder. Preferably, this powder has a density ranging from 2.5 g/cm$^3$ to 3 g/cm$^3$, preferably from 2.6 g/cm$^3$ to 2.8 g/cm$^3$. Preferably, the average size of the powder particles ranges from 0.1 to 100 microns. Preferably, the glass transition temperature of the powder ranges from 500° C. to 700° C. Preferably, the crystallization temperature of the powder ranges from 600° C. to 900° C. Preferably, the melting point of the powder ranges from 900° C. to 1200° C.

In a third step, step c), the powder obtained above is suspended in a solvent and dispersed using a dispersant in order to obtain a slurry. Preferably, the solvent is ethanol. Preferably, the solids content of the suspension ranges from 50% to 60% by weight, relative to the weight of the suspension. Preferably, the dispersant is sodium polyacrylate.

In a fourth step, step d), a thickening agent is added to the slurry. Preferably, this thickening agent is an acrylic emulsion. This thickening agent makes it possible to increase the viscosity of the slurry. The thickening agent also makes it possible to avoid sedimentation or flotation of the pore-forming agent particles, in the case where a pore-forming agent is added, as described below.

In a fifth step, step e), the mixture obtained in d) is poured into a mold then dried to give a "cake". Preferably, the drying is carried out at room temperature.

In a sixth step, step f), the "cake" obtained in e) is heated at a temperature of about 600° C. in order to obtain a "green body". This heat treatment allows organic additives, such as the dispersant, the thickening agent and the possible pore-forming agents added to be removed. This green body has macropores.

In a last step, step g), the green body obtained in f) is treated at a temperature ranging from 600° C. to 1100° C., preferably from 900° C. to 1100° C., in order to obtain partial or total crystallization of the composition. The latter treatment makes it possible to obtain a bulk porous, crystalline or partially crystalline or else glass-ceramic structure.

Figure 1:
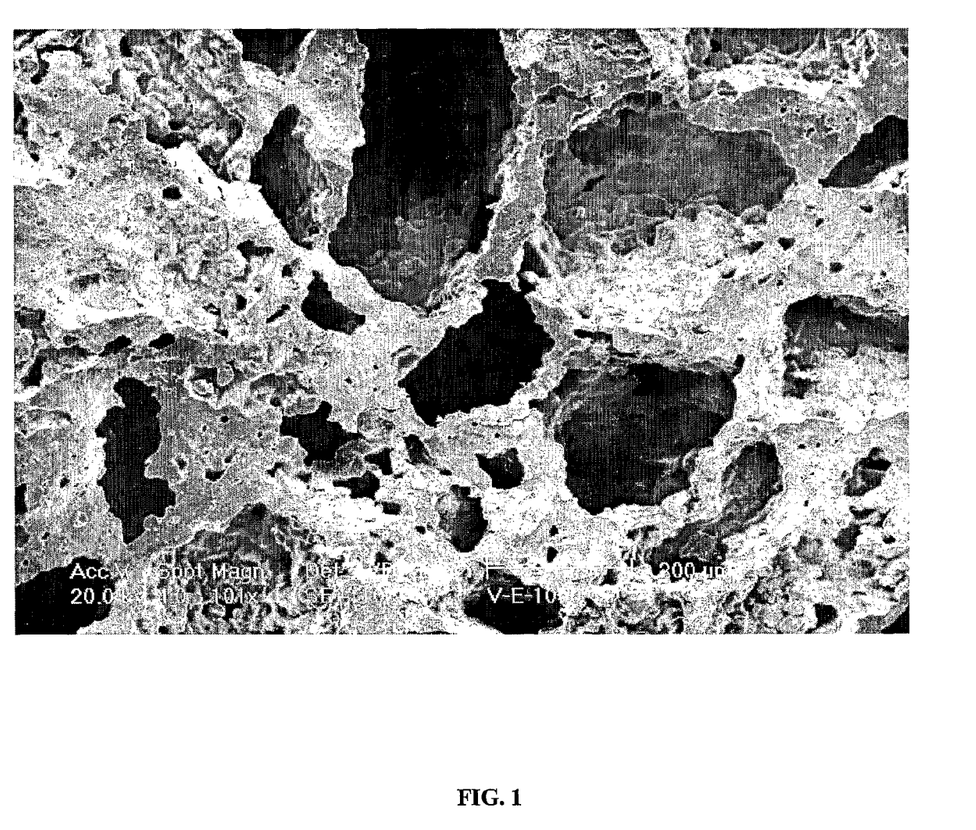
FIGS. 1, 2 and 3 are photographs, taken with an FEI XL30 environmental scanning electron microscope, at magnifications of ×101, ×500 and ×3000 respectively, of a composition obtained according to the method of the invention, in which the treatment in step g) was carried out 1100° C.
Figure 2:
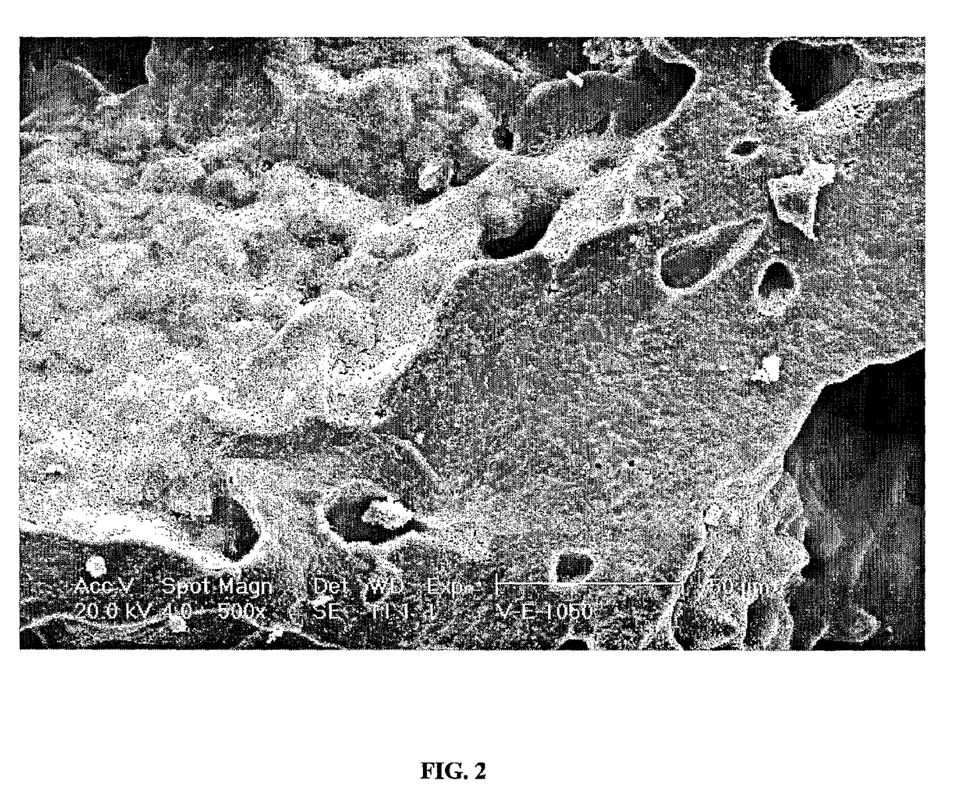
Figure 3:
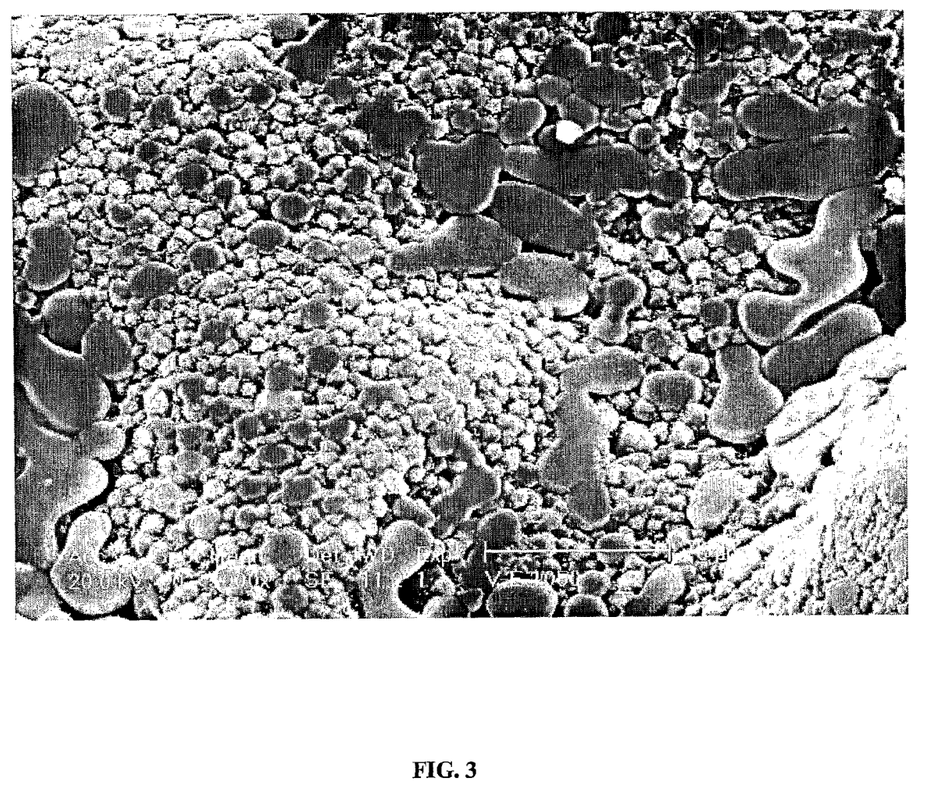

In an embodiment of the method of the invention, the green body is treated at 900° C. The structure of the final composition may be observed in FIGS. 1 to 3. A multitude of different size pores can be seen. The final composition then has a degree of porosity of about 76%, measured according to the geometric method.

In another embodiment of the method of the invention, the green body is treated at 1000° C. The final composition then has a degree of porosity of about 64%, measured according to the geometric method.

Figure 4:
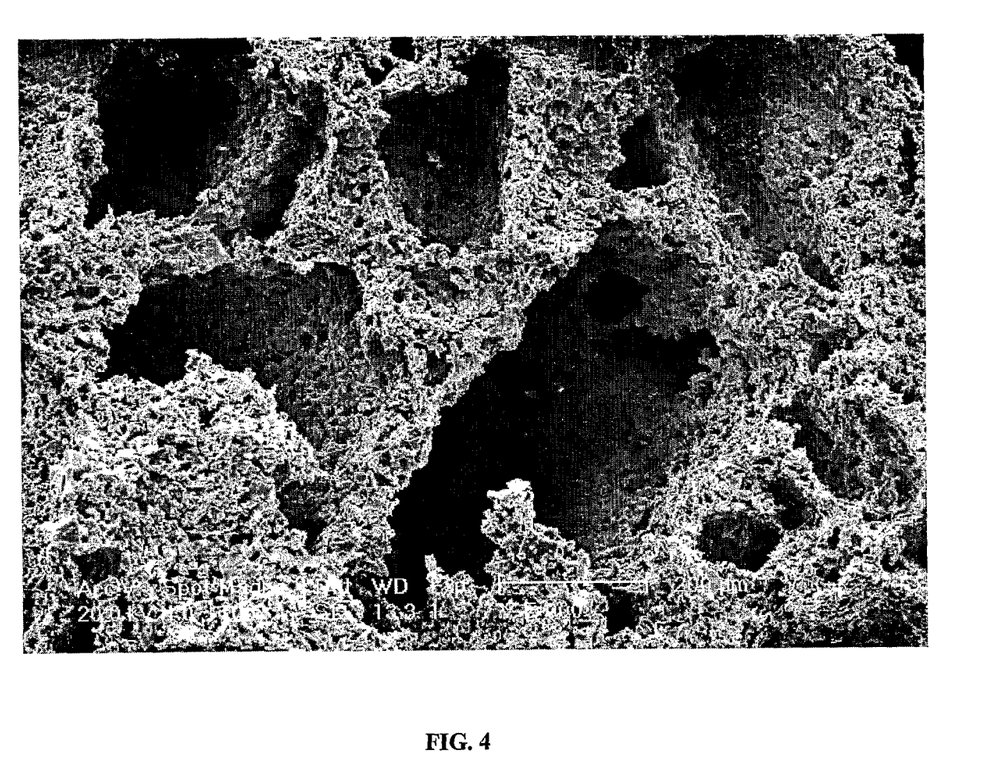
FIGS. 4, 5 and 6 are photographs, taken with an FEI XL30 environmental scanning electron microscope, at magnifications of ×101, ×500 and ×3000 respectively, of a composition obtained according to the method of the invention, in which the treatment in step g) was carried out 900° C.
Figure 5:
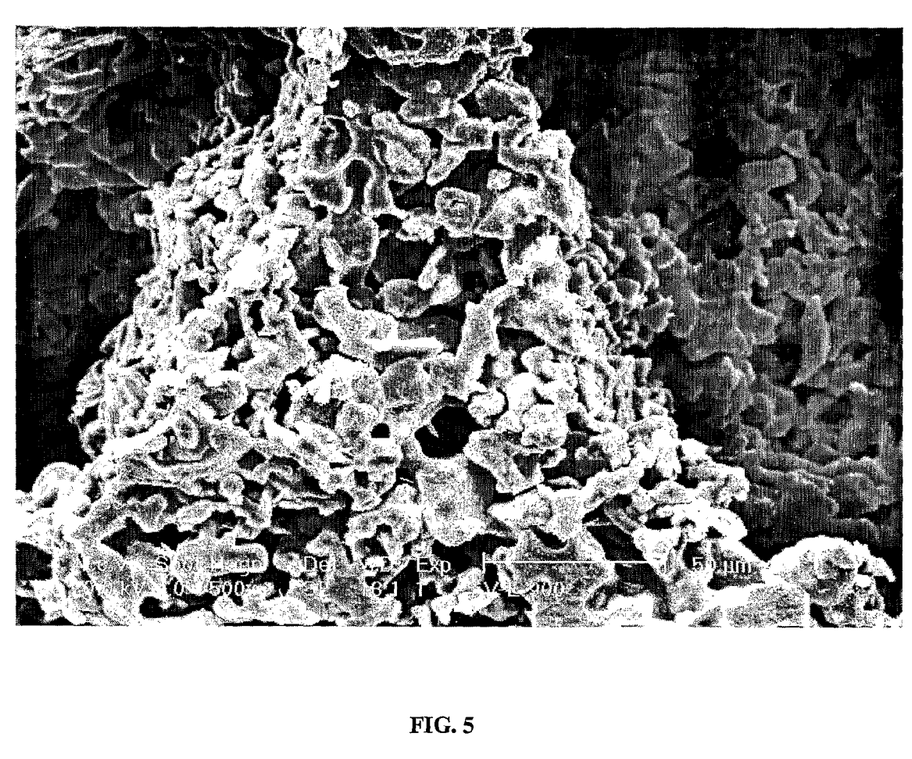
Figure 6:
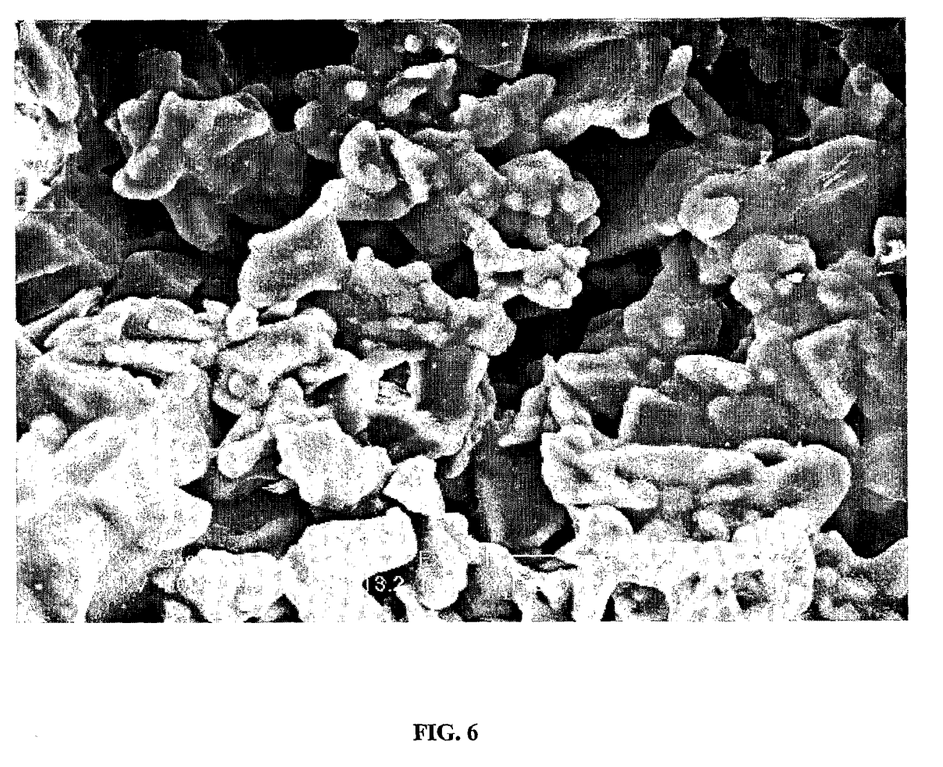

In another embodiment of the method of the invention, the green body is treated at 1100° C. The structure of the final composition may be observed in FIGS. 4 to 6. It can be seen that this structure is more dense than that of FIGS. 1 to 3. The final composition then has a degree of porosity of about 60%, measured according to the geometric method.

In a preferred embodiment of the method according to the invention, a pore-forming agent is added to the slurry with mixing, between step c) and step d). The term "pore-forming agent" is understood to mean a compound that is introduced into the mixture in the form of particles, these particles then degrading at high temperature to leave voids, otherwise known as pores, within the mixture. Preferably, the pore-forming agent is added in an amount ranging from 1% to 80% by volume, more preferably from 50% to 80% by volume, relative to the total volume of the slurry. Preferably, the pore-forming agent is chosen from a mixture of saccharose and starch, polyethylene glycol and mixtures thereof. Preferably, the mixture of saccharose and starch is made up of 80% by weight of saccharose and 20% by weight of starch, relative to the weight of the mixture. Preferably, the size of the particles of the pore-forming agent is less than or equal to 1250 microns.

In a preferred embodiment of the invention, the pore-forming agent consists of a mixture of two particle size populations. Preferably, this mixture consists of 70% by volume, relative to the total volume of the mixture, of pore-forming agents with particle sizes of less than 630 microns and of 30% by volume, relative to the total volume of the mixture, of pore-forming agents with particle sizes ranging from 630 to 1250 microns.

Thus, preferably, the composition according to the invention has macropores created by the degradation of the particles of pore-forming agent.

Whatever the degree of porosity obtained, the mechanical properties of the composition according to the invention are particularly good, especially the compressive strength. Indeed, due to the particular method for preparing compositions according to the invention, the walls of the interconnections are joined together well.

In particular, the compressive strength of the compositions according to the invention is much higher than that of compositions of the prior art based on hydroxyapatite and tricalcium phosphate.

After the heat treatment, the green body may be cut up in order to give the bone implant its definitive shape. The block, or implant, is then cleaned with alcohol in an ultrasonic bath, then packaged in a clean room and sterilized by γ-irradiation.

Another subject of the present invention is a composition such as above, treated with a solution of physiological fluid with an ionic composition close to that of human plasma and a pH ranging from 7 to 8, preferably from 7.25 to 7.42.

Preferably, the ionic composition of this physiological fluid is the following:

$Na^+$: 142.0 mmol/l;
$K^+$: 5.0 mmol/l;
$Mg^{2+}$: 1.5 mmol/l;
$Ca^{2+}$: 2.5 mmol/l;
$Cl^-$: 147.8 mmol/l;
$HCO_3^-$: 4.2 mmol/l;
$HPO_4^{2-}$: 1.0 mmol/l and
$SO_4^{2-}$: 0.5 mmol/l.

Preferably, the composition according to the invention is immersed in this solution at about 37° C. for a duration which may possibly range from 1 to 10 days. The development of a hydroxyapatite layer on the surface of the composition is observed during this immersion. A change in the microstructure of the composition is also observed via the creation of nanopores, the average diameter of these nanopores being less than or equal to 1 micron, preferably ranging from 100 to 300 nanometers.

Thus, in a preferred embodiment of the invention, the composition is treated with a solution of physiological fluid having an ionic composition close to that of human plasma and a pH ranging from 7 to 8, preferably from 7.25 to 7.42, and has a crystallized hydroxyapatite layer on its surface. More preferably, this treated composition has nanopores, the average diameter of these nanopores being less than or equal to 1 micron, preferably ranging from 100 to 300 nanometers.

Figure 7:
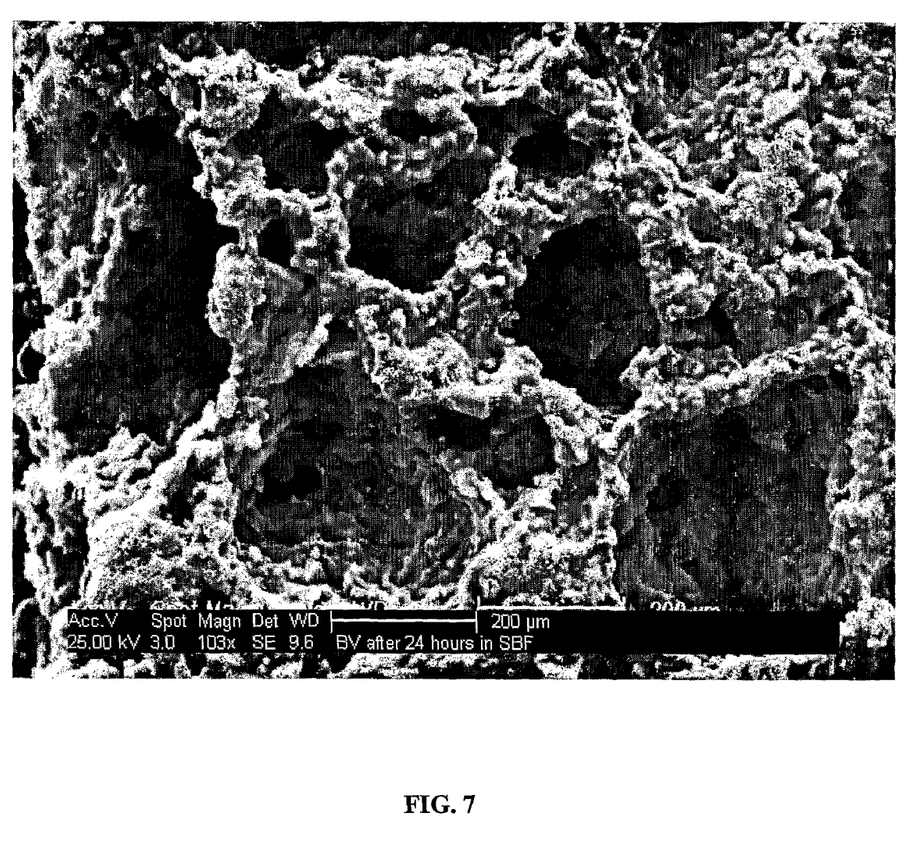
FIGS. 7 and 8 are photographs taken with an FEI XL30 environmental scanning electron microscope, at magnifications of ×103 and ×5054 respectively, of a composition obtained according to the method of the invention, in which the treatment in step g) was carried out at 1100° C., then treated in a solution of physiological fluid for 24 h.
Figure 8:
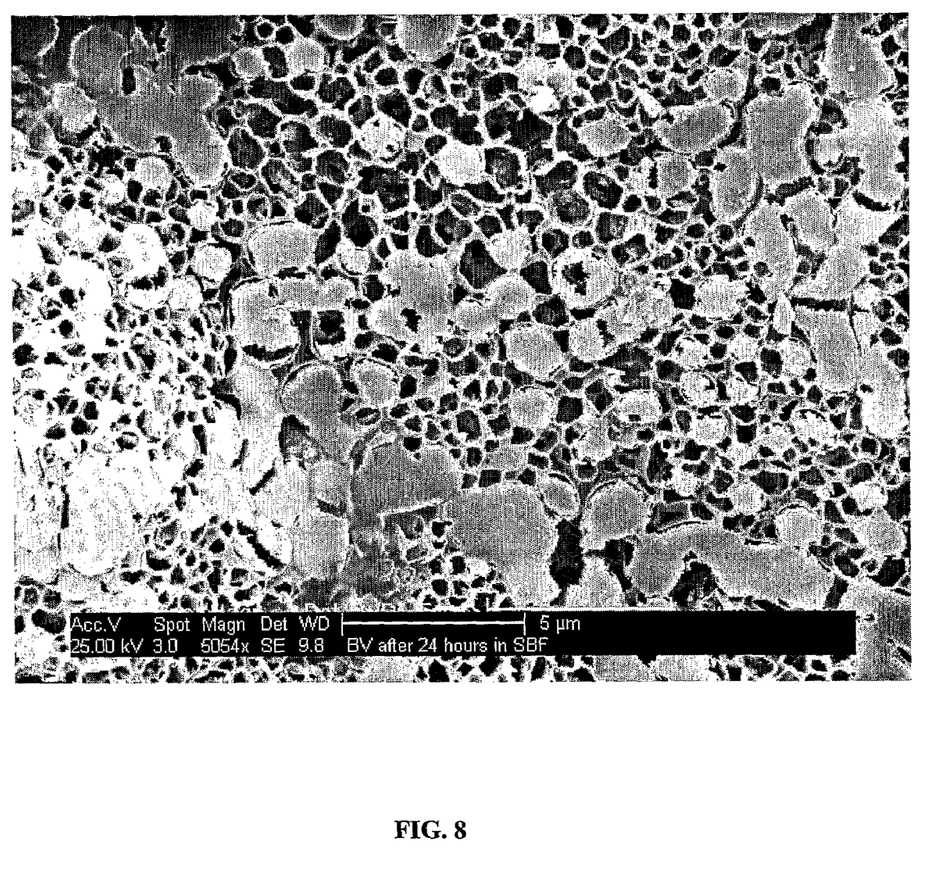

In FIGS. 7 and 8, the structure of a composition can be seen that was obtained according to the method of the invention, in which the treatment in step g) was carried out at 1100° C., then immersed in a solution of physiological fluid with an ionic composition, as described above, for 24 h. The formation of a hydroxyapatite layer on the surface of the composition (FIG. 7) and also the formation of nanopores having an average diameter less than 1 micron (FIG. 8) can be seen.

An example illustrating the present invention will now be given.

EXAMPLE 1

According to the Invention

A composition comprising 45% by weight of $SiO_2$, relative to the total weight of the composition, 24.5% by weight of CaO, relative to the total weight of the composition, 24.5% by weight of $Na_2O$, relative to the total weight of the composition and 6% by weight of $P_2O_5$, relative to the total weight of the composition was prepared conventionally by melting.

100 g of this composition were ground and sieved in order to obtain a powder. The characteristics of the powder were:
density (g/cm³): 2.75;
particle diameter (microns): 5;
glass transition temperature $T_g$ (° C.): 538;
crystallization temperature $T_c$ (° C.): 777; and
melting temperature $T_m$ (° C.): 1060.

200 g of a slurry with the following characteristics were prepared from this powder:
amount of powder (by weight): 50%;
dispersant: sodium polyacrylate;
amount of dispersant (by weight): 0.5%;
thickening agent: acrylic emulsion;
amount of thickening agent (by weight): 2 to 3%;
pore-forming agent: polyethylene glycol;
amount of pore-forming agent (by volume): 80%;
size of the particles of pore-forming agent: mixture of 70% of sizes less than 630 microns and 30% of sizes ranging from 630 microns to 1250 microns; and
solvent: ethanol.

The slurry was prepared with ethanol and dispersed then mixed in a mechanical mixer (ball mill) into polyethylene powder compacts. Next the polyethylene glycol was added, then the thickening agent.

The mixture was then poured into a mold to give, after drying at room temperature, a cake which was then demolded. The cake was then treated at 600° C. to remove the organic additives, namely the dispersant, the thickening agent and the pore-forming agent. The green body was then treated at a temperature of 1100° C. A bulk porous, crystalline composition was obtained having the following characteristics:

The degree of porosity of the final composition was 75%, measured according to the geometric method.

The compressive strength of the final composition was 7 MPa, measured according to the method described in the present application.

The average diameter of the macropores was 100-1250 microns.

The average diameter of the micropores was less than 5 microns.

A bone substitute, or implant, was cut out from this bulk crystalline composition without the latter crumbling.

By way of comparison, a bone substitute made of 70% by weight of hydroxyapatite, relative to the total weight of the substitute and 30% by weight of β-tricalcium phosphate, relative to the total weight of the substitute has a compressive strength of around 1.5 MPa, measured according to the method described in the present application, for an overall degree of porosity of 73%, measured according to the geometric method and for an average pore diameter strictly less than 600 microns.

The invention claimed is:

1. A bulk porous, crystalline or partially crystalline composition comprising at least $SiO_2$, CaO, $Na_2O$ and $P_2O_5$, comprising micropores and macropores, characterized in that:
   the degree of porosity ranges from 50% to 80%, preferably from 60 to 75%, measured by geometric method;
   the average diameter of the macropores ranges from 100 to 1250 microns, preferably from 150 microns to 300 microns;
   the average diameter of the micropores is less than or equal to 5 microns; and
   the compressive strength ranges from 7 MPa to 70 MPa.

2. The composition as claimed in claim 1, characterized in that it comprises, in addition, a component chosen from $K_2O$, MgO, $Al_2O_3$, $CaF_2$, $B_2O_3$ and mixtures thereof.

3. The composition as claimed in claim 1, characterized in that $SiO_2$ is present in the composition in an amount ranging from 40% to 55% by weight, relative to the total weight of the composition, CaO is present in the composition in an amount ranging from 15% to 25% by weight, relative to the total weight of the composition, $Na_2O$ is present in the composition in an amount ranging from 15% to 25% by weight, relative to the total weight of the composition and $P_2O_5$ is present in the composition in an amount ranging from 1% to 9% by weight, relative to the total weight of the composition.

4. The composition as claimed in claim 3, characterized in that the composition is made of 45% by weight of $SiO_2$, relative to the total weight of the composition, 24.5% by weight of CaO, relative to the total weight of the composition, 24.5% by weight of Na$_2$O, relative to the total weight of the composition and 6% by weight of P$_2$O$_5$, relative to the total weight of the composition.

5. The composition as claimed in claim 1, characterized in that it has a compressive strength ranging from 25 MPa to 70 MPa.

6. The composition as claimed in claim 1, characterized in that it has a compressive strength of about 7 MPa, for a degree of porosity, measured according to the geometric method, of about 75%.

7. The composition as claimed in claim 1, characterized in that it has a compressive strength of about 70 MPa, for a degree of porosity, measured according to the geometric method, of about 50%.

8. The composition as claimed in claim 1, characterized in that it is treated with a solution of a physiological fluid with an ionic composition close to that of human plasma.

9. The composition as claimed in claim 8, characterized in that the ionic composition of this physiological fluid is the following:
Na$^+$: 142.0 mmol/l;
K$^+$: 5.0 mmol/l;
Mg$^{2+}$: 1.5 mmol/l;
Ca$^{2+}$: 2.5 mmol/l;
Cl$^-$: 147.8 mmol/l;
HCO$_3$$^-$: 4.2 mmol/l;
HPO$_4$$^{2-}$: 1.0 mmol/l and
SO$_4$$^{2-}$: 0.5 mmol/l.

10. The composition as claimed in claim 8, characterized in that it has a hydroxyapatite layer on its surface.

11. The composition as claimed in claim 8, characterized in that it has nanopores, the average diameter of these nanopores being less than or equal to 1 micron, preferably ranging from 100 to 300 nanometers.

12. An implant characterized in that it is made from a composition as claimed in claim 1.

13. A method for preparing a bulk porous, crystalline or partially crystalline composition comprising at least SiO$_2$, CaO, Na$_2$O and P$_2$O$_5$, comprising micropores and macropores, of which the degree of porosity ranges from 50% to 80% measured by the geometric method, the average diameter of the macropores ranging from 100 to 1250 microns, preferably 150 microns to 300 microns, the average diameter of the micropores being less than or equal to 5 microns, and the compressive strength ranges from 7 MPa to 70 MPa, characterized in that it comprises the following steps:

a) a glass based on SiO$_2$, CaO, Na$_2$O and P$_2$O$_5$ is used;
b) the glass from step a) is ground and sieved to obtain a powder;
c) the powder obtained in b) is suspended in a solvent and dispersed using a dispersant in order to obtain a slurry;
d) a thickening agent is added to the slurry obtained in c);
e) the mixture obtained in d) is poured into a mold then dried to give a "cake";
f) the "cake" obtained in e) is heated at a temperature of about 600° C. in order to obtain a "green body"; and
g) the green body obtained in f) is treated at a temperature ranging from 600° C. to 1100° C., preferably from 900° C. to 1100° C., in order to obtain partial or total crystallization of the composition.

14. The method as claimed in claim 13, characterized in that the thickening agent is an acrylic emulsion.

15. The method as claimed in claim 13, characterized in that the green body is treated at 900° C.

16. The method as claimed in claim 13, characterized in that the green body is treated at 1000° C.

17. The method as claimed in claim 13, characterized in that the green body is treated at 1100° C.

18. The method as claimed in claim 13, characterized in that a pore-forming agent is added with mixing to the slurry, between step c) and step d).

19. The method as claimed in claim 18, characterized in that the pore-forming agent is added in an amount ranging from 1% to 80% by volume, more preferably from 50% to 80% by volume, relative to the total volume of the slurry.

20. The method as claimed in claim 18, characterized in that the pore-forming agent is chosen from a mixture of saccharose and starch, polyethylene glycol and mixtures thereof.

21. The method as claimed in claim 18, characterized in that the pore-forming agent consists of a mixture of two particle size populations.

22. The method as claimed in claim 21, characterized in that this mixture consists of 70% by volume, relative to the total volume of the mixture, of pore-forming agents with particle sizes of less than 630 microns and of 30% by volume, relative to the total volume of the mixture, of pore-forming agents with particle sizes ranging from 630 to 1250 microns.

23. A composition capable of being obtained according to the method as claimed in claim 13.

* * * * *